United States Patent [19]

Billig et al.

[11] 4,283,562
[45] Aug. 11, 1981

[54] HYDROFORMYLATION PROCESS USING STABLE RHODIUM CATALYST

[75] Inventors: Ernst Billig; Donald L. Bunning, both of Charleston, W. Va.

[73] Assignee: Union Carbide Corporation, New York, N.Y.

[21] Appl. No.: 88,827

[22] Filed: Oct. 26, 1979

[51] Int. Cl.$^3$ .............................................. C07C 45/50
[52] U.S. Cl. .................................................. 568/454
[58] Field of Search ................................ 568/454, 451

[56] References Cited

U.S. PATENT DOCUMENTS

| | | | |
|---|---|---|---|
| 3,527,809 | 9/1970 | Pruett et al. | 260/604 HF |
| 3,644,446 | 2/1972 | Booth et al. | 260/429 R |
| 4,151,209 | 4/1979 | Paul et al. | 260/604 HF |

FOREIGN PATENT DOCUMENTS

| | | | |
|---|---|---|---|
| 2904782 | 8/1979 | Fed. Rep. of Germany | 260/604 HF |
| 1228201 | 6/1967 | United Kingdom | 260/604 HF |

OTHER PUBLICATIONS

Falbe, "Carbon Monoxide in Organic Synthesis", pp. 18–22, (1970), Spring-Verlag, N.Y.

Primary Examiner—Werren B. Lone
Attorney, Agent, or Firm—Reynold J. Finnegan

[57] ABSTRACT

In a rhodium-catalyzed hydroformylation process which produces aldehydes from olefins, the stability of a rhodium catalyst complexed with carbon monoxide and a phosphine ligand is improved by the use of a ligand selected from a branched chain alkyldiphenylphosphine, a branched chain dialkylphenylphosphine, a cycloalkyldiphenylphosphine and a dicycloalkylphenylphosphine.

11 Claims, 2 Drawing Figures

HYDROFORMYLATION PROCESS USING STABLE RHODIUM CATALYST

FIELD OF THE INVENTION

This invention relates to an improved process for the rhodium-catalyzed hydroformylation of olefins, particularly alpha-olefins, to produce the corresponding aldehydes; and more particularly to an improved process for the hydroformylation of alpha-olefins to produce the corresponding aldehydes using rhodium complex catalysts whose stability is improved by the use of branched chain alkylphenylphosphine or branched chain cycloalkylphenylphosphine.

BACKGROUND OF THE INVENTION

Processes for forming an aldehyde by the reaction of an olefin with carbon monoxide and hydrogen have been known as hydroformylation processes or oxo processes. For many years, all commercial hydroformylation reactions employed cobalt carbonyl catalysts which required relatively high pressures (often on the order of 100 atmospheres or higher) to maintain catalyst stability.

U.S. Pat. No. 3,527,809, issued Sept. 8, 1970 to R. L. Pruett and J. A. Smith, discloses a significantly new hydroformylation process whereby alpha-olefins are hydroformylated with carbon monoxide and hydrogen to produce aldehydes in high yields at low temperature and pressures, where the normal to iso-(or branched-chain) aldehyde isomer ratio of the product aldehydes is high. This process employs certain rhodium complex catalysts and operates under defined reaction conditions to accomplish the olefin hydroformylation. Since this new process operates at significantly lower pressures than required theretofore in the prior art, substantial advantages are realized including lower initial capital investment and lower operating costs. Further, the more desirable straight-chain aldehyde isomer can be produced in high yields.

The hydroformylation process set forth in the Pruett and Smith patent noted above includes the following essential reaction conditions:

(1) A rhodium complex catalyst which is a complex combination of rhodium with carbon monoxide and a triorganophosphorus ligand. The term "complex" means a coordination compound formed by the union of one or more electronically rich molecules or atoms capable of independent existence with one or more electronically poor molecules or atoms, each of which is also capable of independent existence. Triorganophosphorus ligands whose phosphorus atom has one available or unshared pair of electrons are capable of forming a coordinate bond with rhodium.

(2) An alpha-olefin feed of alpha-olefinic compounds characterized by a terminal ethylenic carbon-to-carbon bond such as a vinyl group $CH_2=CH-$. They may be straight chain or branched chain and may contain groups or substituents which do not essentially interfere with the hydroformylation reaction, and they may also contain more than one ethylenic bond. Propylene is an example of a preferred alpha-olefin.

(3) A triorganophosphorus ligand such as a triarylphosphine. Desirably each organo moiety in the ligand does not exceed 18 carbon atoms. The triarylphosphines are the preferred ligands, an example of which is triphenylphosphine.

(4) A concentration of the triorganophosphorus ligand in the reaction mixture which is sufficient to provide at least 2, and preferably at least 5, moles of free ligand per mole of rhodium metal, over and above the ligand complexed with or tied to the rhodium atom.

(5) A temperature of from about 50° to about 145° C., preferably from about 60° to about 125° C.

(6) A total hydrogen and carbon monoxide pressure which is less than 450 pounds per square inch absolute (psia), preferably less than 350 psia.

(7) A maximum partial pressure exerted by carbon monoxide no greater than about 75 percent based on the total pressure of carbon monoxide and hydrogen, preferably less than 50 percent of this total gas pressure.

It is known in the prior art that rhodium hydroformylation catalysts, such as hydrido carbonyl tris (triphenylphosphine) rhodium, are deactivated by certain extrinsic poisons which may be present in any of the gases fed to the reaction mixture. See, for example, G. Falbe, "Carbon Monoxide in Organic Synthesis", Springer-Verlag, New York, 1970. These poisons (X), termed virulent poisons, are derived from materials such as sulfur-containing compounds (e.g., $H_2S$, COS, etc.), halogen-containing compounds (e.g. HCl, etc.), cyano-containing compounds (e.g. HCN, etc.), and the like, and can form Rh-X bonds which are not broken under mild hydroformylation conditions. If one removes such poisons from the materials fed to the reaction mixture, to below 1 part per million (ppm), one would expect therefore that no such deactivation of the catalyst would occur. However, it has been found that such is not the case. For example, when very clean gases (<1 ppm extrinsic poisons) were used in the hydroformylation of propylene and a gas recycle technique (described in commonly-assigned, copending U.S. application Ser. No. 776,934, filed Mar. 11, 1977 now U.S. Pat. No. 247,486) was employed, under the following conditions:

temperature (°C.): 100
CO partial pressure (psia): 36
$H_2$ partial pressure (psia): 75
olefin partial pressure (psia): 40
ligand/rhodium mole ratio: 94 the catalyst activity decreased at a rate of 3% per day (based on the original activity of the fresh catalyst). It appears therefore that even the substantially complete removal of extrinsic poisons does not prevent such catalyst deactivation.

Copending, commonly-assigned U.S. patent application Ser. No. 762,336, filed Jan. 25, 1977 now abandoned, in favor of continuation U.S. application Ser. No. 151,293, filed May 19, 1980, indicates that the deactivation of rhodium hydroformylation catalysts under hydroformylation conditions in the substantial absence of extrinsic poisons is due to the combination of the effects of temperature, phosphine ligand:rhodium mole ratio, and the partial pressures of hydrogen and carbon monoxide and is termed an intrinsic deactivation. It is further disclosed therein that this intrinsic deactivation can be reduced or substantially prevented by establishing and controlling and correlating the hydroformylation reaction conditions to a low temperature, low carbon monoxide partial pressure and high free triarylphosphine ligand: catalytically-active rhodium mole ratio. More specifically, this copending application discloses a rhodium-catalyzed hydroformylation process for producing aldehydes from alpha-olefins including the steps of reacting the olefin with hydrogen and carbon monoxide in the presence of a rhodium complex catalyst consisting essentially of rhodium complexed with carbon monoxide and a triarylphosphine, under certain defined reaction conditions, as follows:

(1) a temperature of from about 90° to about 130° C.;
(2) a total gas pressure of hydrogen, carbon monoxide and alpha-olefin of less than about 400 psia;
(3) a carbon monoxide partial pressure of less than about 55 psia;
(4) a hydrogen partial pressure of less than about 200 psia;
(5) at least about 100 moles of free triarylphosphine ligand for each mole of catalytically active rhodium metal present in the rhodium complex catalyst; and controlling and correlating the partial pressure of carbon monoxide, the temperature and the free triarylphosphine:catalytically active rhodium mole ratio to limit the rhodium complex catalyst deactivation to a maximum determined percent loss in activity per day, based on the initial activity of the fresh catalyst. By "catalytically active rhodium" is meant the rhodium metal in the rhodium complex catalyst which has not been deactivated. The amount of rhodium in the reaction zone which is catalytically active may be determined at any given time during the reaction by comparing the conversion rate to product based on such catalyst to the conversion rate obtained using fresh catalyst. The manner in which the carbon monoxide partial pressure, temperature and free triarylphosphine:catalytically active rhodium mole ratio should be controlled and correlated to thus limit the deactivation of the catalyst is illustrated in detail in said application Ser. No. 762,336.

It has been observed that the presence of n-alkyldiarylphosphines (for example, n-propyldiphenylphosphine or ethyldiphenylphosphine) in the rhodium-catalyzed hydroformlation of the alpha-olefin propylene inhibits catalyst productivity; i.e., the rate at which the desired product aldehydes are formed. Specifically, the addition of small amounts of propyldiphenylphosphine or ethyldiphenylphosphine to rhodium hydroformylation solutions (i.e., 250 ppm rhodium and 12% by weight triphenylphosphine in a mixture of butyraldehydes and butyraldehyde condensation products) markedly reduced the rate of production of butyraldehydes from propylene, compared to the rate obtained in the absence of the alkyldiarylphosphines. However, copending, commonly-assigned U.S. patent application Ser. No. 762,335, filed Jan. 25, 1977 now abandoned, in favor of continuation U.S. application Ser. No. 140,830, filed on Apr. 16, 1980, discloses that the stability of such rhodium complex catalysts can be significantly enhanced by providing an n-alkyldiarylphosphine in the reaction medium. More specifically, said application Ser. No. 762,335 discloses improving the stability of the catalyst by providing in the liquid reaction medium containing the catalyst an amount of an n-alkyldiarylphosphine ligand; and controlling the hydroformylation reaction conditions as follows:

(1) a temperature of from about 100° to about 140° C.;
(2) a total gas pressure of hydrogen, carbon monoxide and alpha-olefin of less than about 450 psia;
(3) a carbon monoxide partial pressure of less than about 55 psia;
(4) a hydrogen partial pressure of less than about 200 psia;
(5) at least about 75 moles of total free phosphine ligand for each mole of catalytically-active rhodium metal present in the rhodium complex catalyst. However, a disadvantage of using such n-alkyldiarylphosphines is that they substantially retard the rate of the hydroformylation reaction.

U.S. Pat. No. 3,644,446 discloses hydrido carbonyl complexes of rhodium and iridium with biphyllic ligands of the formula

wherein E is As, Sb, P, Bi or P(O)$_3$; and R is hydrogen, C$_{1-10}$ alkyl or C$_{6-10}$ aryl. The patentees generally indicate that such complexes have utility as hydroformylation catalysts.

U.S. Pat. No. 4,151,209 discloses a process for hydroformylating an olefin in the presence of a rhodium complex catalyst comprising rhodium in complex combination with carbon monoxide and a triorganophosphorus ligand, wherein progressive deactivation of the catalyst, as well as loss of the ligand species through by-product formation, are reduced by continuously stripping the liquid reaction medium to a degree such that the content of high-boiling organophosphorus by-products therein is maintained at a low level such that the ratio of phosphorus contained in said high-boiling by-products to phosphorus contained in the ligand present in the reaction medium does not exceed about 0.2.

SUMMARY OF THE INVENTION

It has now been found that branched alkyl- and cycloalkyldiphenylphosphine and branched dialkyl- and dicycloalkylphenylphosphine ligands provide substantially more stable catalysts while retarding the rate of the hydroformylation reaction far less than the analogous n-alkyldiphenylphosphine ligands. This result is unexpected to the extent one skilled in the art would have predicted catalyst stability based on the basicity of the ligand; i.e., while catalyst stability increases with ligand basicity in the order triphenylphosphine and n-alkyldiphenylphosphines, the branched alkyldiphenylphosphines are less basic but yield catalysts which are more stable than those derived from their straight chain analogues.

In summary therefore, the present invention comprises an improved rhodium-catalyzed hydroformylation process for the production of aldehydes from olefins employing a rhodium catalyst complexed with carbon monoxide and a phosphine ligand, where the stability of the rhodium complex catalyst is substantially improved by employing as the phosphine ligand a branched alkyldiphenylphosphine, a cycloalkyldiphenylphosphine, a branched dialkylphenylphosphine or a dicycloalkylphenylphosphine. In addition to substantially improving the stability of the rhodium complex catalyst, these ligands retard the rate of hydroformylation reaction far less than the n-alkyldiphenylphosphines of the prior art.

DESCRIPTION OF THE PREFERRED EMBODIMENTS

In its broadest aspects, the present invention is an improvement in a rhodium-catalyzed process for hydroformylating an olefin to produce aldehydes having one more carbon atom than the olefin, which process includes the steps of reacting the olefin with hydrogen and carbon monoxide, in a liquid reaction medium which contains a soluble rhodium complex catalyst consisting essentially of rhodium complexed with carbon monoxide and a phosphine ligand selected from the group consisting of branched alkyldiphenylphosphines, branched dialkylphenylphosphines, cycloalkyldiphenylphosphines and dicycloalkylphenylphosphines. The particular phosphine ligand employed may be selected based on several considerations, as discussed below.

Figure 1:
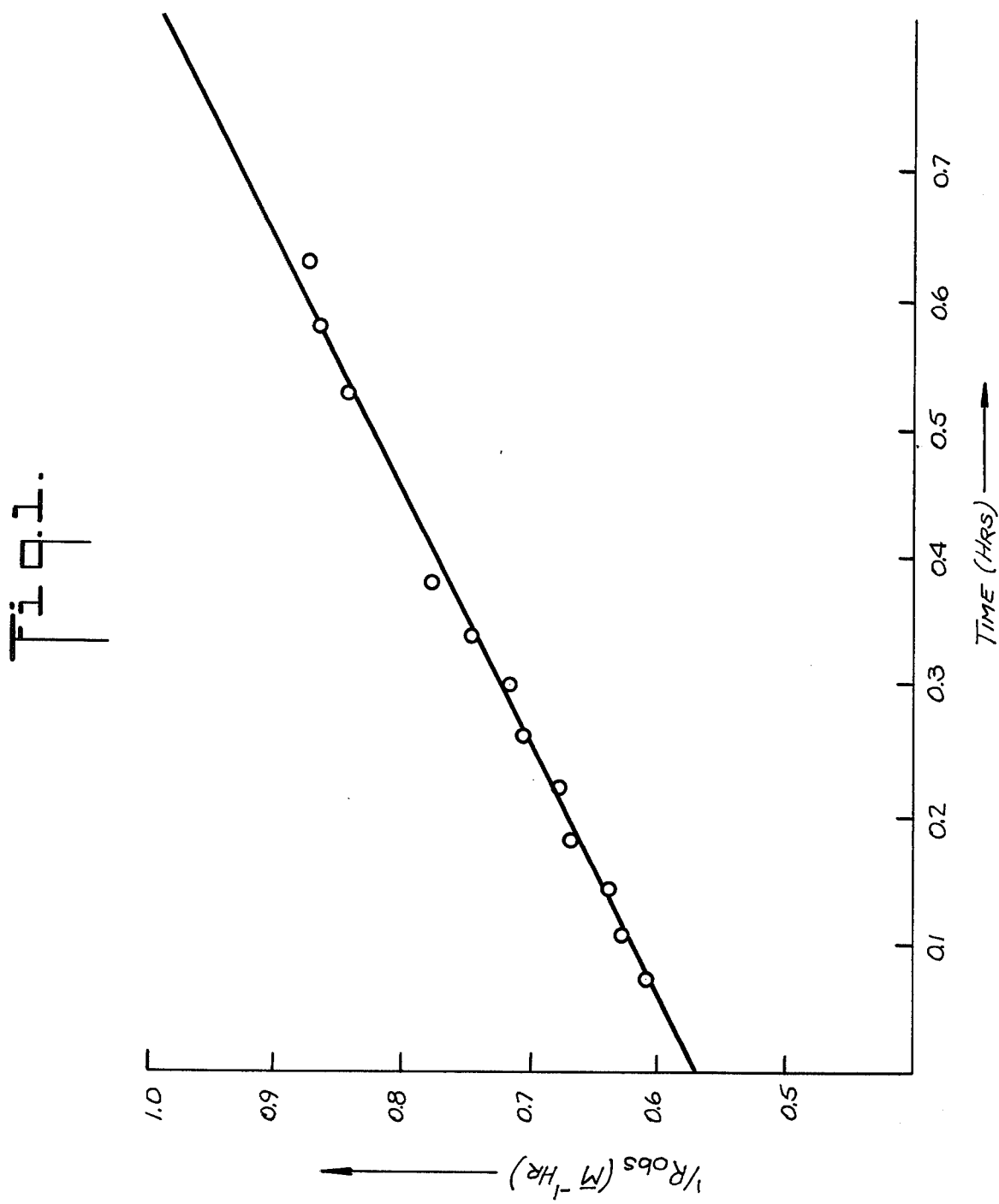
FIG. 1 is a plot of the reciprocal of the production rate of aldehyde versus time employing triphenylphosphine ligand.

Different ligands have different effects on the initial rate (i.e., using undeactivated catalyst) of hydroformylation and on the rate at which the rhodium complex catalyst becomes deactivated under hydroformylation reaction conditions. These effects may be determined as follows. By carrying out the hydroformylation at sufficiently low ligand concentrations, such as below 1 weight percent based on the weight of the liquid reaction medium, and by continuously monitoring the rate of hydroformylation, the decline in hydroformylation rate (or loss in catalyst activity) may be observed in a convenient laboratory time frame. The decline in rate appears to be kinetically consistent with a second order process inasmuch as the reciprocal of the observed rate is inversely proportional to time. This procedure has been used to identify these effects for certain ligands. More specifically, into a 100 ml stainless steel autoclave, equipped with a magnetic stirrer and externally heated, was charged 15 ml of a catalyst solution containing 250 ppm rhodium, introduced as dicarbonyl rhodium acetylacetonate, and 0.64 weight% triphenylphosphine in dimethylformamide. The autoclave was purged with nitrogen and brought to an internal temperature of 80° C. 75 psia of a premixed gas consisting of $C_3H_6$: $CO$:$H_2$ in a 1:1:1 molar ratio was then added and the same reaction temperature was maintained with stirring. The average rate of hydroformylation, in gram-moles/liter/hr, was determined over each successive period of time necessary for a 5 psi pressure drop to occur. The results are shown in FIG. 1 of the drawings, where the reciprocal rate ($\overline{M}$=average observed rate, gram-moles/liter/hr) is shown to be proportional to the time of reaction. Expressed mathematically, if $[Rh]_a$ represents the active rhodium in solution at time t, then $$d[Rh]_a/dt = -k_2[Rh]_a^2 = \text{observed rate}$$

The second order deactivation rate constant, $k_2$, can then be calculated by conventional means from the slope of the plot of rate $^{-1}$ versus time, and the initial rate of reaction from the y-axis intercept. Thus, the stabilizing influence of any given ligand against the intrinsic loss of catalyst activity may be investigated in the same manner and subsequently correlated with its corresponding second order deactivation rate constant. In other words, the particular phosphine ligand may accordingly be selected depending upon the starting olefin, the rate of reaction desired, the temperature of reaction, the ratio of reactants, etc., in the same manner as described above.

Generally, the amount of the phosphine ligand present in the liquid reaction medium is from about 0.25 to about 25 percent by weight, based upon the total weight of the liquid reaction medium. The particular amount of phosphine ligand in the reaction medium will depend on several factors such as the particular olefin reacted, the particular phosphine ligand employed, the reaction conditions, the desired rate of reaction, etc. Generally, however, amounts falling within the aforementioned range will provide satisfactory results. The preferred amount of phosphine ligand in the liquid reaction medium is from about 1 to about 15 percent by weight, based on the total weight of the liquid reaction medium.

The phosphine ligand employed in the present invention may be represented by the following formula (I):

$$R_nP\ Ph_{3-n} \qquad (I)$$

wherein Ph is phenyl, n is an integer of 1 or 2 and R represents a branched alkyl group or a cycloalkyl group.

In formula (I), when R is a branched alkyl group, it may be a secondary or tertiary alkyl group having from 3 to 9 carbon atoms, such as isopropyl, sec-butyl, tert-butyl, sec-amyl, tert-amyl, iso-octyl, and the like. The preferred branched alkyl groups are secondary alkyl groups having from 3 to 6 carbon atoms, with isopropyl being most preferred.

In formula (I) above, when R is a cycloalkyl group, it may be a cycloalkyl group having from 5 to 12 carbon atoms, such as cyclopentyl, cyclohexyl, cyclooctyl, and the like. The preferred cycloalkyl group is cyclohexyl.

Generally, the particular phosphine ligand which is employed in the practice of the invention may be selected by obtaining its second order deactivation rate constant (with higher positive numbers resulting in faster deactivation) and initial rate of reaction, as described above, which, in turn, will provide guidelines for the selection of the appropriate ligand, depending upon the results desired.

The rhodium complex catalyst consists essentially of rhodium complexed with carbon monoxide and the phosphine ligand. The terminology "consists essentially of" is not meant to exclude, but rather to include, hydrogen complexed with the rhodium, in addition to carbon monoxide and the phosphine ligand. However, this language is meant to exclude other materials in amounts which poison or deactivate the catalyst. This catalyst is normally soluble in the liquids which may be used as a solvent in the reaction, and the most desirable catalyst is free of contaminants such as rhodium-bound halogen such as chlorine and like species.

Generally, according to the present invention, the hydroformylation reaction conditions are controlled within the following ranges:

(1) a temperature of from about 90° to 130° C.;
(2) a total gas pressure of hydrogen, carbon monoxide and olefin of less than about 250 psia;
(3) a carbon monoxide partial pressure of less than about 30 psia;
(4) a hydrogen partial pressure of less than about 200 psia; and
(5) at least about 3 moles of total phosphine ligand for each mole of catalytically-active rhodium metal present in the rhodium complex catalyst.

The total amount of phosphine ligand present in the liquid reaction medium should be sufficient to provide the above noted minimum number of moles of total phosphine ligand per mole of catalytically-active rhodium metal present in the rhodium complex catalyst and to generate active catalyst and maintain catalyst stability. It should be noted that the upper limit is dictated largely by commercial and economic considerations and that higher mole ratios of free phosphine:catalytically-active rhodium metal favor catalyst stability. With this in mind, it is preferred that the total amount of phosphine ligand be at least about 6 moles for each mole of catalytically-active rhodium.

The rhodium complex catalyst composed of rhodium complexed with hydrogen, carbon monoxide and phosphine ligand may be formed by methods known in the art. For example, a preformed stable crystalline solid of rhodium hydridocarbonyltris (isopropyldiphenylphosphine), $RhH(CO) [P(C_6H_5)_2(i-C_3H_7)]_3$ may be introduced into the reaction medium. This material may be formed for example, by a method similar to that disclosed in Brown, et al., *Journal of the Chemical Society,* 1970, pages 2753–2764. Alternatively, a rhodium catalyst precursor such as $Rh_2O_3$, $Rh_4(CO)_{12}$, or $Rh_6(CO)_{16}$ and the like may be introduced into the reaction medium along with the phosphine ligand. In a preferred embodiment, rhodium dicarbonyl acetylacetonate is employed as a rhodium precursor. In either event, the active rhodium complex catalyst is formed in the reaction medium under the conditions of hydroformylation.

The amount of catalyst present in the reaction medium should be as a minimum that amount which is necessary to catalyze the hydroformylation of the olefin to form the product aldehydes. Generally, the rhodium concentration in the reaction medium can range from about 25 ppm to about 1200 ppm, preferably from about 50 ppm to about 400 ppm, of catalytically active rhodium calculated as the free metal.

The process of the present invention is expected to be useful for the hydroformylation of olefins having up to 20 carbon atoms including both terminal and internal olefins. The process of the present invention is particularly useful for the hydroformylation of alpha-olefins having from 2 to 5 carbon atoms, including ethylene, propylene, 1-butene, 1-pentene and the like, and therefore this constitutes a preferred embodiment. The process of the present invention is especially useful for the hydroformylation of propylene to form butyraldehydes, and hence this presently constitutes the most preferred embodiment. Typical internal olefins include 2-butene, 2-hexene and the like. The olefins used in the process of the invention may be straight-chain or branched-chain and may contain groups or substituents which do not essentially interfere with the course of the hydroformylation reaction.

The amount of olefin fed to the reaction depends on several factors, such as the size of the reactor, the temperature of reaction, the total pressure, the amount of catalyst, etc. In general, the higher the olefin concentration is in the reaction medium, the lower usually will be the catalyst concentration that can be used to achieve a given conversion rate to aldehyde products in a given size of reactor. Since partial pressures and concentration are related, the use of higher olefin partial pressure leads to an increased proportion of the olefin in the product stream leaving the reaction mixture. Further, since some amount of saturated hydrocarbon may be formed by hydrogenation of the olefin, it may be necessary to purge part of the product gas stream in order to remove this saturated product before any recycle to the reaction zone, and this would be a source of loss for the unreacted olefin contained in the product gas stream. Hence, it is necessary to balance the economic value of the olefin lost in such a purge stream against the economic savings associated with lower catalyst concentration.

The temperature of reaction, as noted above, may vary from about 90° to about 130° C., with the lower temperatures favoring catalyst stability and the higher temperatures favoring higher rates of reaction. The particular temperature employed in the reaction will of course depend upon the desired stability and rate of reaction, but generally, by controlling the temperature within this range, the advantages of the present invention can be attained.

The process of the present invention operates at a low total pressure of hydrogen, carbon monoxide and alpha-olefin of less than about 250 psia. The minimum total pressure of these gases is not particularly critical and is limited predominantly only by the amount of reaction gases necessary to obtain the desired rate of reaction.

The make-up gases fed to the reaction medium would include the olefin, carbon monoxide and hydrogen, usually. As pointed out previously, extrinsic poisons such as sulfur and sulfur-containing compounds, as well as halogens and halogencontaining compounds, and the like, should be excluded from the make-up gases, since it is known that such materials poison the catalyst and can deactivate the catalyst rather rapidly. Hence, it is desirable to reduce the amount of such poisons in all gases fed to the reaction. Of course, the amount of such poisons that can be tolerated is determined by the maximum acceptable rate of loss of activity of the catalyst. If it is possible to permit some small amount of such poisons and still obtain a catalyst of desired stability, then such small amounts can be tolerated. It is generally desirable to reduce the amounts of such poisons in the make-up gases to below one part per million. This can be accomplished by methods known in the art.

The partial pressure of carbon monoxide has a significant effect on the stability of the catalyst, and should generally be less than about 30 psia. Of course, the particular partial pressure employed will depend upon the desired stability and rate of reaction. As a general rule, lower carbon monoxide partial pressure provide more stable catalysts. It is preferred according to the process of the invention that the partial pressure of carbon monoxide be from about 5 psia to about 10 psia. The minimum partial pressure of carbon monoxide is not critical in that it is limited predominantly only by the desired rate of reaction and the possibility of olefin hydrogenation occurring.

It is disclosed in U.S. Pat. No. 3,527,809 that the normal to iso aldehyde isomer ratio of the aldehyde products decreases as the partial pressure of carbon monoxide increases. Generally, therefore the partial pressure of carbon monoxide should be low. However, the phosphine ligands employed in the present invention do lower the normal to iso isomer ratio as compared to triphenylphosphine, thus diminishing to an extent the direct effect of the partial pressure of carbon monoxide.

The time of reaction, or residence period of the olefin in the reaction zone, is generally that time which is sufficient to hydroformylate the ethylenic bond of the olefin. As a general rule, the residence period in the reaction zone can vary from about several minutes to about several hours in duration and as is apparent, this variable will be influenced, to a certain extent, by the reaction temperature, the choice of olefin and catalyst, the total amount of phosphine ligand, the total pressure, the partial pressures exerted by carbon monoxide and hydrogen, the conversion rate and other factors. As a general rule, it is desirable to achieve the highest possible conversion rate for the smallest amount of catalyst employed. Of course, the ultimate determination of a conversion rate is influenced by many factors including the economics of the process. A substantial advantage of the present invention is that catalyst stability is substantially improved while retarding conversion rates far less than the n-alkyldiphenylphosphine ligands.

It is preferred to effect the process of the invention in a liquid phase in the reaction zone which contains the rhodium complex catalyst in a solvent therefor. The particular solvent employed is not critical and may be selected from, for example, inert organic solvents such as dimethylformamide, acetophenone, higher boiling liquid aldehyde condensation products, toluene, and the like. The preferred solvents are the higher boiling liquid aldehyde condensation products.

By the term "higher boiling liquid aldehyde condensation products" as used herein is meant the complex mixture of high boiling liquid products which results from the condensation reactions of some of the aldehyde products of the process of the invention. Such condensation products can be preformed or produced in situ in the present process. The rhodium complex catalyst is soluble in these relatively high boiling liquid aldehyde condensation products while exhibiting excellent stability over extended periods of continuous hydroformylation. These higher boiling liquid aldehyde condensation products are more fully described, and methods for preparing the same are more fully described, in commonly-assigned U.S. Pat. No. 4,148,830 the disclosure of which is hereby incorporated herein by reference and reference can be made to this patent for a more detailed description.

If desired, the process of the invention may employ the gas recycle technique described in commonly-assigned, copending U.S. Application Ser. No. 776,934, filed Mar. 11, 1977 the disclosure of which is hereby incorporated herein by reference. If the aforementioned higher boiling liquid aldehyde condensation products are employed as the reaction solvent, the liquid body in the reaction zone will normally comprise a homogeneous mixture containing the soluble catalyst, free phosphine ligand, the solvent, the product aldehydes, reaction by-products and the reactants, olefin, carbon monoxide and hydrogen.

The relative proportion of each reaction product in solution is controlled by the amount of gas passing through the solution. Increasing this amount decreases the equilibrium aldehyde concentration and increases the rate of by-product removal from solution. The by-products include the higher boiling liquid aldehyde condensation products. The decreased aldehyde concentration leads to a reduction in the rate of formation of the by-products.

The dual effect of this increased removal rate and decreased formation rate means that the mass balance in byproducts in the reactor is very sensitive to the amount of gas passing through the liquid body. The gas cycle typically includes make-up quantities of hydrogen, carbon monoxide and olefin. However, the most meaningful factor is the amount of recycle gas returned to the liquid body since this determines the degree of reaction, the amount of product formed and the amount of by-product (as a consequence) removed.

Operation of the hydroformylation reaction with a given flow rate of olefin and synthesis gas (i.e., carbon monoxide and hydrogen) and with a total low amount of gas recycle less than a critical threshold rate results in a high equilibrium aldehyde concentration in solution and hence, in high by-product formation rates.

The rate of removal of by-products in the vapor phase effluent from the reaction zone (liquid body) under such conditions will be low because the low vapor phase effluent flow rate from the reaction zone can only result in a relatively low rate of carry-over of by-products. The net effect is a build-up of by-products in the liquid body solution causing an increase in the solution volume with a consequent loss of catalyst productivity. A purge must therefore be taken from the solution when the hydroformylation process is operated under such low gas flow rate conditions in order to remove by-products and hence maintain a mass balance over the reaction zone.

If however, the gas flow rate through the reaction zone is increased by increasing the gas recycle rate the solution aldehyde content falls, the by-product formation rate is decreased and by-product removal rate in the vapor phase effluent from the reaction zone is increased. The net effect of this change is to increase the proportion of the by-products removed with vapor phase effluent from the reaction zone. Increasing the gas flow rate through the reaction zone still further by a further increase in the gas recycle rate leads to a situation in which by-products are removed in the vapor phase effluent from the reaction zone at the same rate as they are formed, thus establishing a mass balance over the reaction zone. This is the critical threshold gas recycle rate which is the preferred minimum gas recycle rate used in the proces of the invention. If the process is operated with a gas recycle rate higher than this threshold gas recycle rate the volume of the liquid body in the reaction zone will tend to decrease and so, at gas recycle rates above the threshold rate, some of the crude aldehyde by-product mixture should be returned to the reaction zone from the product separation zone in order to keep constant the volume of the liquid phase in the reaction zone.

The critical threshold gas recycle flow rate can be found by a process of trial and error for a given olefin and synthesis gas (the mixture of carbon monoxide and hydrogen) feed rate. Operating at recycle rates below the critical threshold rates will increase the volume of the liquid phase with time. Operating at the threshold rate keeps the volume constant. Operating above the threshold rate decreases the volume. The critical threshold gas recycle rate can be calculated from the vapor pressures at the reaction temperature of the aldehyde or aldehydes and of each of the by-products present.

With the process operating at a gas recycle rate at or greater than the threshold rate, by-products are removed in the gaseous vapors removed from the reaction zone containing the liquid body at the same rate as or faster than they are formed, and thus do not accumulate in the liquid phase in the reaction zone. Under such circumstances, it is unnecessary to purge the liquid body containing the catalyst from the reaction zone in order to remove by-products.

EXAMPLES 1-11

A 100 ml stainless steel autoclave reactor, equipped with a magnetic stirrer and externally heated with two 300 watt band heaters, was connected to a gas manifold. A 15 ml charge of a catalyst solution containing 250 ppm rhodium (calculated as the free metal and introduced as Rh (CO)$_2$ acetylacetonate) and the ligands shown in Table I below (the total ligand/rhodium mole ratio being 10/1) in dimethylformamide as a solvent, was introduced into the autoclave. The reactor was purged with nitrogen and the internal reactor temperature was brought to and maintained at the temperatures shown in Table I below with a proportional temperature controller. 75 psia of a premixed feed gas consisting of $C_3H_6$:CO:$H_2$ at a molar ratio of 1:1:1 was then added to the reactor and the hydroformylation reaction was allowed to proceed with a corresponding pressure drop. The observed rates of the hydroformylation reaction were determined at the successive times required for a 5 psi pressure drop to occur. By plotting the reciprocal of these observed rates, $\overline{M}$/hr (average gram-moles/liter/hour), against time as in FIG. 1 of the drawings, the second order deactivation rate constant and initial hydroformylation rate for each ligand was determined. The results are shown in Table I below.

TABLE I

| Example | Ligand | Reaction Temperature (°C.) | Initial Rate of Hydroformylation ($\overline{M}$/hr) | 2nd Order Deactivation Rate Constant, $k_2$ ($M^{-1}hr^{-2}$) |
|---|---|---|---|---|
| 1 | MePPh$_2$ | 125 | 0.28 | Very small* |
| 2 | n-Bu$_3$P | 125 | 0.58 | $1.46 \times 10^{-3}$ |
| 3 | n-Pr$_2$PPh | 125 | 0.89 | $7.01 \times 10^{-4}$ |
| 4 | n-PrPPh$_2$ | 125 | 3.17 | $1.22 \times 10^{-2}$ |
| 5 | i-PrPPh$_2$ | 100 | 3.34 | $2.55 \times 10^{-3}$ |
| 6 | i-Pr$_2$PPh | 110 | 3.55 | Very small* |
| 7 | $_2$PPh | 100 | 2.52 | Very small* |
| 8 | PPh$_2$ | 100 | 4.28 | $1.08 \times 10^{-2}$ |
| 9 | t-BuPPh$_2$ | 100 | 3.17 | $7.07 \times 10^{-3}$ |
| 10 | Et PPh$_2$ | 125 | 2.07 | $4.14 \times 10^{-3}$ |
| 11 | Ph$_3$P | 100 | 4.24 | $2.33 \times 10^{-2}$ |

Notes:
Ph = phenyl
Me = methyl
Bu = butyl
Pr = propyl

 = cyclohexyl

Et = ethyl
* = smaller than $1.00 \times 10^{-4}$

Examples 1-4, 10 and 11 are included for comparison purposes and are not within the scope of the present invention. The n-alkylphenylphosphine ligands of Examples 1-3 have relatively low deactivation rate constants, indicative of catalyst stability, but significantly the corresponding initial rates of hydroformylation are low. The ligands of Examples 4 and 11 (and to a lesser extent, Example 10), while having relatively high initial hydroformylation rates, exhibit relatively higher deactivation rate constants. However, the secondary and tertiary alkylphenylphosphines and cycloalkylphenylphosphines of Examples 5-9, corresponding to the present invention, exhibited a combination of high initial rates of hydroformylation and good catalyst stability (although the deactivation rate constant of Example 8 is high, its initial rate of hydroformylation is the highest).

From all these examples, it is seen that all the alkylsubstituted phosphines were more stable than triphenylphosphine.

Figure 2:
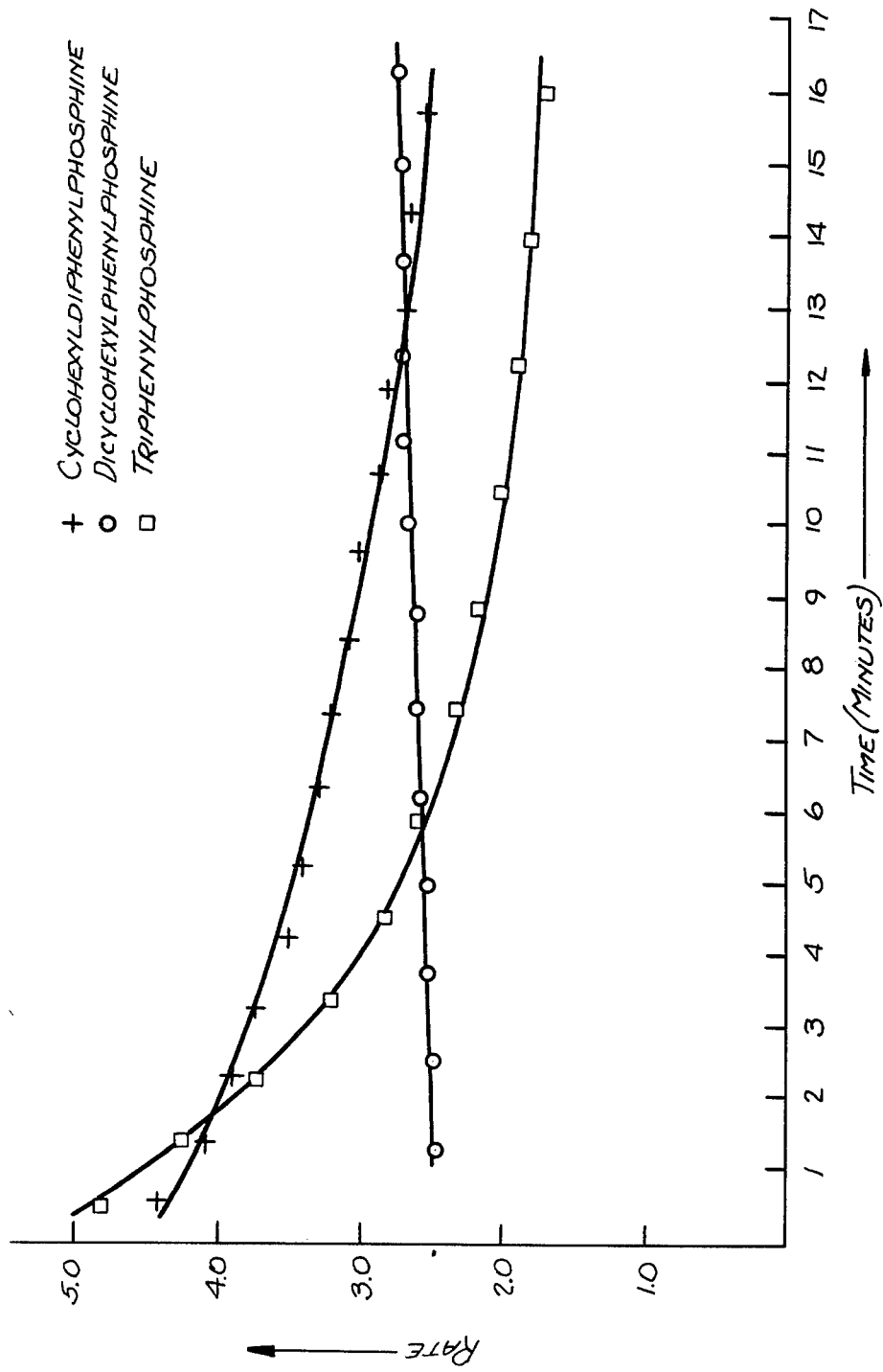
FIG. 2 shows the change in aldehyde production rate with time for several ligands (dicyclohexylphenylphosphine, cyclohexyldiphenylphosphine and triphenylphosphine).

FIG. 2 shows comparative rate profiles versus time for the ligands dicyclohexylphenylphosphine, cyclohexyldiphenylphosphine and triphenylphosphine. It is seen that the monocyclohexyldiphenylphosphine approaches the same initial (undeactivated) rate as triphenylphosphine but that the intrinsic loss in catalytic activity proceeds at a slower rate in the presence of the former ligand.

EXAMPLES 12-15

The procedure of Examples 1-11 was repeated except that the ligands and the conditions shown in Table II below were employed. The average hydroformylation rate, $\overline{M}$/hr (gram-moles/liter/hr), was determined. The aldehyde isomer ratio was determined by gas chromatography of the reaction solution. The results are shown in Table II below. Example 12 is included for comparison purposes only. From the data in Table II, it is seen that the phosphine ligands used in the present invention (Exs. 13-15) provide lower n/i ratios than triphenylphosphine ligand (Ex. 12).

TABLE II

| Example | Ligand | Total Ligand/Rh (molar) | Reaction Temperature (°C.) | Hydroformylation Rate ($\overline{M}$/hr) | normal/iso aldehyde ratio |
|---|---|---|---|---|---|
| 12 | PPh$_3$ | 80 | 110 | 2.05 | 5.35 |
| 13 | t-BuPPh$_2$ | 80 | 110 | 0.91 | 2.81 |
| 14 | i-PrPPh$_2$ | 80 | 110 | 0.62 | 2.12 |
| 15 | $_2$PPh | 65 | 120 | 1.17 | 1.20 |

Notes:

Ph, Bu, Pr and  mean the same as in Table I

What is claimed is:

1. In a process for the hydroformylation of an olefin to produce aldehydes having one more carbon atom than the olefin comprising reacting said olefin with hydrogen and carbon monoxide in a liquid reaction medium which contains a soluble rhodium complex catalyst consisting essentially of rhodium complexed with carbon monoxide and a phosphine ligand and wherein the hydroformylation reaction conditions are controlled to a temperature of from about 90° to about 145° C., a total gas pressure of hydrogen, carbon monoxide and olefin of less than about 450 pounds per square inch absolute, a carbon monoxide partial pressure of less than about 55 pounds per square inch absolute, a hydrogen partial pressure of less than about 200 pounds per square inch absolute, and at least about 6 total moles of said phosphine ligand for each mole of catalytically-active rhodium metal present in the rhodium complex catalyst, the improvement comprising improving the stability of said catalyst against deactivation by employing as said phosphine ligand a phosphine represented by the following formula (I):

$$R_nPPh_{3-n} \qquad (I)$$

wherein R represents a branched chain alkyl group having from 3 to 9 carbon atoms or a cycloalkyl group having from 5 to 12 carbon atoms, n represents an integer of 1 or 2 and Ph represents phenyl.

2. The process of claim 1 wherein said phosphine ligand is present in said liquid reaction medium in an amount of from about 0.25 to about 25 percent by weight, based on the total weight of the liquid reaction medium.

3. The process of claim 1 wherein said olefin is an alpha-olefin having from 2 to 5 carbon atoms.

4. The process of claim 3 wherein said alpha-olefin is propylene, ethylene or 1-butene.

5. The process of claim 1 wherein said olefin is an internal olefin.

6. The process of claim 5 wherein said internal olefin is 2-butene or 2-hexene.

7. The process of claim 1 wherein said phosphine ligand is a secondary-alkylphenylphosphine wherein the alkyl group has from 3 to 6 carbon atoms.

8. The process of claim 7 wherein said phosphine ligand is isopropyldiphenylphosphine or diisopropylphenylphosphine.

9. The process of claim 1 wherein said phosphine ligand is cyclohexyldiphenylphosphine or dicyclohexylphenylphosphine.

10. The process of claim 1 wherein said catalyst is dissolved in a solvent which comprises the high boiling liquid condensation products of said aldehydes.

11. The process of claim 1, wherein the hydroformylation reaction conditions are controlled to a temperature of from about 90° to about 130° C., a total gas pressure of hydrogen, carbon monoxide and olefin of less than about 250 pounds per square inch absolute and a carbon monoxide partial pressure of less than about 30 pounds per square inch absolute.

* * * * *